US00PP23667P2

(12) United States Plant Patent
Kordes

(10) Patent No.: US PP23,667 P2
(45) Date of Patent: Jun. 18, 2013

(54) FLORIBUNDA ROSE PLANT NAMED 'KORLUBAJA'

(50) Latin Name: *Rosa hybrida*
Varietal Denomination: KORlubaja

(75) Inventor: Tim-Hermann Kordes, Klein Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 125 days.

(21) Appl. No.: 13/066,489

(22) Filed: Apr. 14, 2011

(51) Int. Cl.
*A01H 5/00* (2006.01)

(52) U.S. Cl.
USPC ..... Plt./150

(58) Field of Classification Search
USPC ..... Plt./146, 147, 148, 135, 136, 137, Plt./141
See application file for complete search history.

*Primary Examiner* — June Hwu

(57) ABSTRACT

A new and distinct variety of rose with long lasting, novel Tangerine/Peach/Orange flowers, and attractive foliage with good disease resistance. It exhibits upright growth with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORlubaja'.

CROSS REFERENCES AND FEDERAL R&D STATEMENT

There are no cross referenced or related applications. This variety was developed without the aid of any research grant.

BACKGROUND OF THE INVENTION

The new variety of rose plant of the present invention originated from a controlled crossing in a breeding program of two distinct parents during the summer of 1997. The crossing was between 'TANeitber', a non-patented rose and an 'un-named seedling'.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORlubaja'.

SUMMARY OF THE INVENTION

The new rose plant may be distinguished from its seed parent, 'TANeitber' by the following combination of characteristics:

1. The seed parent has very double blooms while 'KORlubaja' has double blooms.
2. The seed parent has semi-glossy foliage while the foliage of 'KORlubaja' has glossy foliage.

The new rose plant may be distinguished from its pollen parent, an 'un-named seedling', by the following combination of characteristics:

1. 'KORlubaja' has apricot orange flowers, while the 'unnamed seedling' has pink flowers.
2. 'KORlubaja' has a bushy growth habit, while the 'unnamed seedling' has a spreading habit.

The objective of the hybridization was to create a new and distinct rose plant with unique qualities, such as:

1. Uniform growth and flowering;
2. Abundant attractive, recurrent flowers;
3. Attractive and abundant foliage; and
3. Resistance to diseases encountered in landscapes and gardens.

This combination of qualities is not present in prior rose cultivars known to the inventor. These objectives have been substantially achieved and in that distinguish 'KORlubaja' from all other varieties of which we are aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORlubaja' was selected in May, 1998 from the seedling beds to be asexually propagated for further evaluation. The first asexual propagation of 'KORlubaja' was done by budding to seedling understocks in July, 1998 at the inventor's nursery in Offenseth-Sparrieshoop, Germany.

This initial and other subsequent propagations conducted in controlled environments demonstrate that 'KORlubaja' reproduces true to type in successive generations of asexual reproduction.

BRIEF DESCRIPTION OF THE DRAWING

The accompanying color drawing shows as true as is reasonably possible to obtain in color photographs of this type, the typical characteristics of the flowers of 'KORlubaja' on a three year old plant.

DETAILED BOTANICAL DESCRIPTION

The following is a description of 'KORlubaja', as observed growing in a nursery during October 2010 in Jackson County, Oreg. on plants of 4 years of age. Color references are made using The Royal Horticultural Society (London, England) Colour Chart, 2001 except where common terms of color are used.

For a comparison, several physical characteristics of the rose variety 'KORravreli', a rose variety from the same inventor described and illustrated in U.S. Plant Pat. No. 15,253 and issued on Oct. 19, 2004 from the same inventor are compared to 'KORlubaja' in Chart 1.

CHART 1

| Characteristic | 'KORlubaja' | 'KORravreli' |
|---|---|---|
| Upper side of flower petal, when flower is one-half open. | Red Group 47C. | Red Group 38D and Yellow Group 2D. |
| Average number of petals per flower. | 20-22 petals. | 70-80 petals |

Parents:

*Seed parent.*—'TANeitber'.

*Pollen parent.*—'Un-named seedling'.

Classification:

*Botanical classification.—Rosa hybrida,* 'KORlubaja'.

*Commercial classification.*—Floribunda rose.

FLOWER AND FLOWER BUD

Blooming habit: Recurrent.

Flower bud:

*Size.*—Upon opening, 35 mm in length from base of receptacle to end of bud and 25-27 mm diameter at its widest point.

*Bud form.*—Short. Pointed ovoid.

*Bud color.*—As sepals first unfold, bud color is Red Group 45C. When ¼ open, the upper surface of petals is Red Group 43C and Red Group 43D and the lower surface is Red Group 43C and Red Group 43D. The guard petals are Red Group 45B and Red Group 45C with intonations of Yellow-Green Group 151C.

*Sepals.*—Size: Average 30-35 mm long×7-9 mm wide. Shape: Sepals generally subulate. Sepal apex is generally cirrose. Weak foliaceous appendages on three of the five sepals. Base is flat at union with receptacle.

*Quantity.*—Five.

*Margins.*—With stipitate glands and numerous short fine white hairs.

*Surface texture.*—Inner side: Covered with numerous fine white hairs. Outer surface: Smooth, with limited numbers of stipitate glands.

*Color.*—Upper surface; Green Group 138B. Lower Surface; Green Group 138B. The middle zone of the lower surface is Yellow-Green Group 144C. The margin is Green Group 137C. Most of the sepals exhibit intonations of Greyed-Purple Group 184B.

Receptacle:

*Surface.*—Smooth.

*Color.*—Green Group 137C with intonations of Greyed-Purple Group 185A.

*Shape.*—Urn-shaped.

*Size.*—10-11 mm (h)×8-9 mm (w).

Peduncle: The inflorescence is a raceme consisting of peduncles, pedicels, and flowers. The inflorescences vary in size from 10-20 cm in width and 8-16 cm in height.

*Surface.*—With fine hairs and stipitate glands.

*Length: Variable, from* 8.0-15 cm in length.

*Diameter.*—4.0 mm average diameter.

*Color.*—Green Group 137C.

*Strength.*—Moderately strong.

*Borne.*—Upright, as a raceme, with 3-5 pedicels per peduncle.

Pedicels:

*Surface.*—With fine hairs and stipitate glands.

*Length.*—40-50 mm average length.

*Diameter.*—1.5-2.5 mm average diameter.

*Color.*—Green Group 137C.

*Strength.*—Moderately strong.

*Borne.*—Most commonly with one flower per pedicel.

Flower bloom:

*Fragrance.*—Little to no fragrance.

*Duration.*—On the plant 4-6 days. Senesced petals drop away cleanly.

*Size.*—Medium sized flower for a garden rose. When open, the average flower diameter is 55-70 mm and the average flower height is 35-40 mm.

*Form.*—Shape of flower when viewed from the side: Upon opening, upper part: Flattened convex. Upon opening, lower part: Flattened convex. Open flower, upper part: Flat to a flattened convex. Open flower, lower part: Flat.

Color:

*Upon opening, petals.*—Outermost petals: Outer Side: Red Group 53C. Inner Side: Red Group 47C. Innermost petals: Outer Side: Red Group 53C. Inner Side: Red Group 47C.

*Upon opening, basal petal spots.*—Basal petal spot, outermost petals: Outer Side: Yellow Group 8A. Inner Side: Yellow-Orange Group 16B. Basal petal spot, innermost petals: Outer Side: Yellow-Orange Group 17C. Inner Side: Yellow-Orange Group 17C.

*After opening, petals.*—Outermost petals: Outer Side: Red Group 55B. Inner Side: Red Group 54B. Innermost petals: Outer Side: Red Group 47B. Inner Side: Red Group 46C.

*After opening, basal petal spots.*—Basal petal spot, outermost petals: Outer Side: Yellow Group 8A. Inner Side: Yellow-Orange Group 16B. Basal petal spot, innermost petals: Outer Side: Yellow-Orange Group 17C. Variegations: Occasional greenish streak of Yellow-Green Group 151C on the guard petals.

General tonality: On open flower Red Group 48A. No change in the general tonality at the end of the $4^{th}$-$5^{th}$ day. Afterwards, general tonality is Red Group 48C.

Petals:

*Petal count.*—Double flowered with approximately 20-22 petals under normal conditions.

*Petal reflex.*—Petals generally not reflexing.

*Petal edge.*—Often, petal margin is undulated and with a point in center of margin.

*Petal shape.*—Rounded to oval. Apex shape is round. Shape of base is rounded.

*Petal size.*—24-28 mm long; 25-40 mm wide.

*Thickness.*—Average.

*Petal arrangement.*—Not formal.

Petaloids: Usually a few present.

*Petaloid count.*—Average of 1-2 per flower.

*Petaloid edge.*—Smooth.

*Petaloid texture.*—Smooth.

*Petaloid shape.*—Deltoid to round. Most commonly folded.

*Petaloid size*.—Petaloids are 15-22 mm long and 12-16 mm wide.

*Petaloid color*.—Color of inner side is Red Purple Group 61C. Color of outer side is Red Group 51A. Basal petal spot on petaloids is Yellow-Orange Group 16B.

Reproductive organs:

*Pistils*.—Average number of pistils. Approximately 12-14 present. Stigmas: Location: Slightly superior in position to anthers. Color: Yellow Group 12B. Styles: Length: 6-8 mm long. Color: Yellow Group 1C. Intonations lacking.

*Stamens*.—Abundant. Approximately 60 - 70 on average and regularly arranged. Anthers: Size: 2-2½ mm long. Color: Margins of anthers are Yellow Group 13A. Center of anther is Green-Yellow Group 160C. As the anthers senesce, color is Gray-Orange Group 164C. Pollen: Generally present. Color: Yellow Group 13A. Filaments: Color: Yellow Group 12A. Length: 5-8 mm.

THE PLANT

Plant growth: Moderate vigor. Upright to bushy habit. When grown as a budded field grown plant the average plant height is 100-120 cm and the average plant width is 70-75 cm.

Stems:

*Stem color*.—Young wood: Green Group 138B. Older wood: Green Group 138B.

*Stem surface*.—Young wood: Moderately smooth. Older wood: Smooth. Roughens slightly with age.

Prickles: Present.

*Incidence*.—7-9 per 10 cm of stem.

*Size*.—Average length: 6-8 mm.

*Color*.—Immature prickles: Greyed-Purple Group 183C. Mature prickles: Greyed-Orange Group 166C. Senescing to Greyed-Brown Group 199C.

*Shape*.—Concave.

*Anthocyanin*.—On younger thorns. Color Greyed-Purple group 183C.

Leaves and leaflets: Normally 7 leaflets on normal leaves in middle of the stem.

*Venation pattern*.—Pyramidal net pattern.

*Leaf size*.—130-150 mm (l)×85-105 mm (w).

*Quantity*.—Very abundant.

*Texture*.—Upper side of leaflet: Semi glossy. Under side of leaflet: Matte, leathery, thick.

*Color, mature foliage*.—Upper Leaf Surface: Green Group 139A. Lower Leaf Surface: Yellow-Green Group 146A.

*Color, juvenile foliage*.—Upper Leaf Surface: Green Group 139A. Lower Leaf Surface: Yellow-Green Group 146A.

*Anthocyanin intonation*.—Present. Location: Intonations present on juvenile leaf margins, petiole, undersides of leaflets, rachis, and petiole rachis. Greyed Purple Group 183C.

Stipules:

*Size*.—18-20 mm long. One per compound leaf.

*Stipule color*.—Green-Group 138A. Anthocyanin: Greyed-Purple Group 183C.

*Presence of stipitate glands*.—Present on margins.

*Shape*.—Apex: pointed. Base: Flat.

Petiole:

*Length*.—20-25 mm.

*Diameter*.—1.5 mm.

*Petiole color*.—Green Group 138A.

*Underneath*.—Smooth.

*Stipitate glands*.—Moderate numbers of stipitate glands on margins. Anthocyanin: Greyed-Purple Group 138A.

Petiole rachis:

*Length*.—15-25 mm.

*Diameter*.—1.5 mm.

*Color*.—Green Group 138A Most with Intonations of Purple Group 138A. Anthocyanin present on all surfaces Purple Group 138A.

*Margins*.—Smooth.

*Prickles*.—1-2 per entire leaf.

*Stipitate glands*.—Moderate numbers of stipitate glands on margins.

Leaflets:

*Size*.—Average size of the terminal leaflet is 55-65 mm (l)×35-40 mm (w).

*Shape*.—Base: Ovate. Apex: Acute.

*Margins*.—Serrated.

*Texture*.—Thick, Leathery.

Hips/seed formation: Observed. Size: of hip is 15-20 mm diameter. Color of mature hip is Orange-Red Group 34B. Surface texture is glabrous. Seed formation not observed to date.

Winter hardiness: To date, the variety has been grown successfully in Zone 5.

Disease resistance: Above average resistance to Powdery mildew (*Sphaerotheca pannosa*), rust (*P. disciflorum*), and *Botrytis* (*Botrytis cinerea*) diseases under normal growing conditions.

I claim:

1. A new and distinct variety of rose plant, as described and illustrated herein.

* * * * *

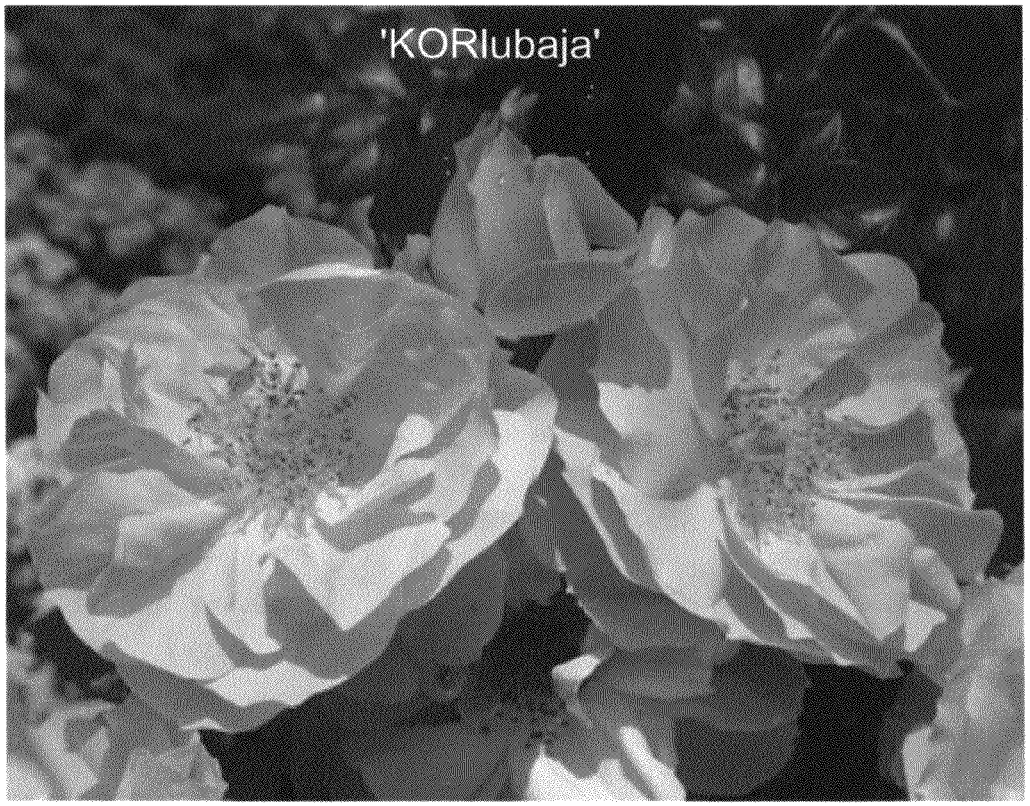
'KORlubaja'